(12) United States Patent
Lidgren et al.

(10) Patent No.: US 7,417,077 B2
(45) Date of Patent: Aug. 26, 2008

(54) COMPOSITION FOR AN INJECTABLE BONE MINERAL SUBSTITUTE MATERIAL

(75) Inventors: Lars Lidgren, Lund (SE); Malin Nilsson, Lund (SE)

(73) Assignee: Bone Support AB, Tolarp (SE)

( * ) Notice: Subject to any disclaimer, the term of this patent is extended or adjusted under 35 U.S.C. 154(b) by 281 days.

(21) Appl. No.: 10/333,026

(22) PCT Filed: Jul. 16, 2001

(86) PCT No.: PCT/SE01/01627

§ 371 (c)(1),
(2), (4) Date: Oct. 22, 2003

(87) PCT Pub. No.: WO02/05861

PCT Pub. Date: Jan. 24, 2002

(65) Prior Publication Data

US 2004/0048947 A1   Mar. 11, 2004

(30) Foreign Application Priority Data

Jul. 17, 2000   (SE) .................................. 0002676

(51) Int. Cl.
*A61F 2/02* (2006.01)
*A01N 57/26* (2006.01)
*A61K 33/42* (2006.01)

(52) U.S. Cl. ................. 523/115; 523/116; 424/489; 424/602

(58) Field of Classification Search ................. 523/115, 523/116; 424/602
See application file for complete search history.

(56) References Cited

U.S. PATENT DOCUMENTS

| | | | |
|---|---|---|---|
| 4,001,323 A | 1/1977 | Felder et al. | |
| 4,139,605 A | 2/1979 | Felder et al. | |
| 4,348,377 A | 9/1982 | Felder et al. | |
| 4,487,766 A | 12/1984 | Mach | |
| 4,619,655 A | 10/1986 | Hanker et al. | |
| 4,752,479 A | 6/1988 | Briggs et al. | |
| 4,994,442 A | 2/1991 | Gil et al. | |
| 5,073,362 A | 12/1991 | Blaszkiewicz et al. | |
| 5,149,368 A * | 9/1992 | Liu et al. ................... | 424/602 |
| 5,342,441 A | 8/1994 | Mandai et al. | |
| 5,360,823 A | 11/1994 | Griffel et al. | |
| 5,447,711 A | 9/1995 | Almen et al. | |
| 5,462,722 A | 10/1995 | Liu et al. | |
| 5,549,380 A | 8/1996 | Lidgren et al. | |
| 5,614,206 A | 3/1997 | Randolph et al. | |
| 5,650,108 A | 7/1997 | Nies et al. | |
| 5,681,873 A | 10/1997 | Norton et al. | |
| 5,695,742 A | 12/1997 | Felder et al. | |
| 5,797,873 A | 8/1998 | Franz et al. | |
| 5,866,100 A | 2/1999 | Tournier et al. | |
| 5,871,549 A | 2/1999 | Jayashankar et al. | |
| 5,965,772 A | 10/1999 | Desantis | |
| 6,018,095 A | 1/2000 | Lerch et al. | |
| 6,071,982 A | 6/2000 | Wise et al. | |
| 6,075,067 A | 6/2000 | Lidgren | |
| 6,080,801 A | 6/2000 | Draenert et al. | |
| 6,206,957 B1 | 3/2001 | Driessens et al. | |
| 6,231,615 B1 | 5/2001 | Preissman | |
| 6,251,139 B1 | 6/2001 | Lin et al. | |
| 6,309,420 B1 | 10/2001 | Preissman | |
| 6,586,009 B1 | 7/2003 | Lidgren | |
| 6,596,904 B1 | 7/2003 | Dunn et al. | |
| 6,689,375 B1 | 2/2004 | Wahlig et al. | |
| 6,706,069 B2 | 3/2004 | Berger | |
| 6,723,334 B1 | 4/2004 | McGee et al. | |
| 6,897,339 B2 | 5/2005 | Turchetta et al. | |
| 2001/0012968 A1 | 8/2001 | Preissman | |
| 2001/0051670 A1 | 12/2001 | Goupil et al. | |
| 2002/0055143 A1* | 5/2002 | Bell et al. ................... | 435/69.1 |
| 2002/0076378 A1 | 6/2002 | Wolfe et al. | |

(Continued)

FOREIGN PATENT DOCUMENTS

DE   44 09 610 A1   9/1995

(Continued)

OTHER PUBLICATIONS

"Calcium phosphate cements: action of setting regulators on the properties on the β-tricalcium phosphate-monocalcium phosphate cements," Amir A. Mirtchi et al., *Biomaterials* (1989), 10(9), pp. 634-638.

(Continued)

*Primary Examiner*—Tae H Yoon
(74) *Attorney, Agent, or Firm*—Finnegan, Henderson, Farabow, Garrett & Dunner, LLP (57) ABSTRACT

The invention refers to an injectable composition for a bone mineral substitute material, which comprises a dry powder mixed with an aqueous liquid. The powder comprises a first reaction component comprising a calcium sulphate hemihydrate with the capability of being hardened to calcium sulphate dihydrate when reacting with said aqueous liquid; a second reaction component, which comprise a calcium phosphate with the capability of being hardened to a calcium phosphate cement when reacting with said aqueous liquid; and at least one accelerator for the reaction of said first and/or second reaction component with said aqueous liquid. A method of producing an injectable bone mineral substitute material is also provided, wherein the composition is mixed in a closed mixing and delivery system for delivery.

45 Claims, 3 Drawing Sheets

U.S. PATENT DOCUMENTS

| | | | |
|---|---|---|---|
| 2003/0050702 | A1 | 3/2003 | Berger |
| 2003/0055512 | A1 | 3/2003 | Genin et al. |
| 2003/0161858 | A1* | 8/2003 | Lidgren ............... 424/423 |
| 2004/0048947 | A1 | 3/2004 | Lidgren et al. |
| 2004/0049202 | A1 | 3/2004 | Berger |
| 2004/0151751 | A1 | 8/2004 | Cooper |
| 2004/0244651 | A1 | 12/2004 | Lemaitre et al. |
| 2005/0023171 | A1 | 2/2005 | Delaney et al. |
| 2005/0119746 | A1 | 6/2005 | Lidgren |
| 2005/0241535 | A1 | 11/2005 | Bohner |
| 2005/0251149 | A1 | 11/2005 | Wenz |
| 2005/0257714 | A1 | 11/2005 | Constanz et al. |
| 2005/0287071 | A1 | 12/2005 | Wenz |
| 2006/0004358 | A1 | 1/2006 | Serhan et al. |
| 2006/0036211 | A1 | 2/2006 | Solsberg et al. |
| 2006/0041033 | A1 | 2/2006 | Bisig et al. |
| 2007/0041906 | A1 | 2/2007 | Lidgren et al. |
| 2007/0161943 | A1 | 7/2007 | Lidgren et al. |

FOREIGN PATENT DOCUMENTS

| | | |
|---|---|---|
| EP | 0 023 992 A1 | 2/1981 |
| EP | 0 109 310 B1 | 5/1984 |
| EP | 0 308 364 A2 | 3/1989 |
| EP | 0 495 284 A1 | 7/1992 |
| EP | 0 639 382 A1 | 2/1995 |
| EP | 0 639 382 B1 | 2/1995 |
| EP | 0 520 690 B1 | 11/1995 |
| EP | 0 807 432 B1 | 11/1997 |
| EP | 0 950 420 A2 | 10/1999 |
| ES | 2 178 556 | 12/2002 |
| JP | 1-139516 | 6/1989 |
| SE | 8903538 | 4/1991 |
| WO | WO 85/01727 | 4/1985 |
| WO | WO 87/05521 | 9/1987 |
| WO | WO 89/03695 | 5/1989 |
| WO | WO 91/00252 | 1/1991 |
| WO | 91/17722 | 11/1991 |
| WO | WO 96/39202 | 12/1996 |
| WO | WO 97/47334 | 12/1997 |
| WO | WO 99/17710 | 4/1999 |
| WO | WO 99/62570 | 12/1999 |
| WO | WO 00/02597 | 1/2000 |
| WO | WO 00/45867 | 8/2000 |
| WO | WO 01/34216 | 5/2001 |
| WO | WO 03/041753 | 5/2003 |
| WO | WO 03/053488 | 7/2003 |
| WO | WO 2004/000374 | 12/2003 |

OTHER PUBLICATIONS

"Effects of Sulfate Ions on the in Vitro Properties of βB-TCP—MCPM—Water Mixtures. Preliminary in Vivo Results," M. Bohner et al., *Ceramic Transations*, vol. 48 (1995), pp. 245-259.

M. Nilsson et al., "New Perspectives of Bioactives Calcium Phosphate Cements for Biomedical Applications", Research Centre in Biomedical Engineering, Dept. of Material Science and Metallurgy, Universitat Politècnica de Catalunya, Avda, Diagonal 647, Barcelona, E-08028, Spain, pp. 95-99, Nov. 2000.

Database WPI: Week 198928, Derwent Publications Ltd., JP 1-139516, Jun. 1989.

International Search Report for PCT/SE01/00789 dated Jul. 9, 2001, related to U.S. Appl. No. 10/257,561.

Database WPI: Week 200138, Derwent Publications Ltd., WO 2001/34216.

Database WPI: Week 199734, Derwent Publications Ltd., EP 0 807 432 B1.

Database WPI: Week 199126, Derwent Publications Ltd., SE 8903538.

Database WPI: Week 199433, Derwent Publications Ltd., London, GB: AN 1994-269325 & JP 61 99623 A (Lion Corp et al.), Jul. 19, 1994.

International Preliminary Examination Report for PCT/SE02/02428 dated Mar. 16, 2004, related to U.S. Appl. No. 10/499,023.

International Search Report for PCT/SE02/02428 dated Apr. 4, 2003, related to U.S. Appl. No. 10/499,023.

International Preliminary Examination Report for PCT/SE2004/000328 dated Aug. 30, 2005, related to U.S. Appl. No. 10/547,671.

International Search Report for PCT/SE2004/000328 dated Jun. 8, 2004, related to U.S. Appl. No. 10/547,671.

International Preliminary Examination Report for PCT/SE01/01627 dated Oct. 14, 2002, related to U.S. Appl. No. 10/333,026.

International Search Report for PCT/SE01/01627 dated Dec. 18, 2001, related to U.S. Appl. No. 10/333,026.

International Preliminary Examination Report for PCT/SE01/00789 dated Jan. 11, 2002, related to U.S. Appl. No. 10/257,561.

International Search Report for PCT/SE01/01627 dated Jul. 9, 2001, related to U.S. Appl. No. 10/257,561.

Bohner, M. "New hydraulic cements based on α-tricalcium phosphate-calcium sulfate dihydrate mixtures," *Biomaterials* (2004) 25, 741-749.

Cabañas, M. V. "Setting Behavior and in Vitro Bioactivity of Hydroxyapatite/Calcium Sulfate Cements," *Chem. Mater.* (2002) 14, 3550-3555.

Nilsson, M. et al. "Characterization of a novel calcium phosphate/sulphate bone cement," *J. Biomedical Materials Research* (2002) 61(4), 600-607.

Copending U.S. Appl. No. 10/257,561, Office Action dated Mar. 28, 2007.

Copending U.S. Appl. No. 10/257,561, Office Action dated Sep. 5, 2006.

Office Action in copending U.S. Appl. No. 10/499,023 dated Oct. 4, 2007.

Office Action in copending U.S. Appl. No. 10/257,561 dated Oct. 15, 2007.

English-language translation of SE 8903538, "Implant material and method for the manufacture thereof," 2001.

English-language translation of JP 1-139516, 1989.

* cited by examiner

COMPOSITION FOR AN INJECTABLE BONE MINERAL SUBSTITUTE MATERIAL

TECHNICAL FIELD

The present invention relates to an injectable composition for a bone mineral substitute material with the capability of being hardened in a body fluid in vivo. Furthermore, the invention relates to a method of producing such a material.

BACKGROUND ART

During the last decade, the number of fractures related to osteoporosis, i.e. reduced bone mass and changes in microstructure leading to an increased risk of bone fractures, has almost doubled. Due to the continuously increasing average life time it is estimated that by 2020 people over 60 years of age will represent 25% of Europe's population and that 40% of all women over 50 years of age will suffer from an osteoporotic fracture.

With the aim to reduce or eliminate the need for bone grafting, research has been made to find a suitable artificial bone mineral substitute. Presently, at least the following bone mineral substitutes are used for the healing of bone defects and bone fractures, namely calcium sulphates, as for instance Plaster of Paris, calcium phosphates, as for instance hydroxylapatite, and polymers, as for instance polymethylmetacrylate (PMMA).

Calcium sulphate (Plaster of Paris), $CaSO_4 \cdot \frac{1}{2}H_2O$, was one of the first materials investigated as a substitute for bone grafts. Studies have been undertaken since 1892 to demonstrate its acceptance by the tissues and rapid rate of resorbtion It has been concluded that Plaster of Paris implanted in areas of subperiosteal bone produces no further untoward reaction in the tissue than normally is present in a fracture. Regeneration of bone in the area of subperiosteal resection occurs earlier than when an autogenous graft is used. Plaster of Paris does not stimulate osteogenesis in the absence of bone periosteum. The new bone growing into Plaster of Paris is normal bone. No side effects attributable to the implantation of Plaster of Paris have been noted in adjacent tissues or in distant organs. However, Plaster of Paris has the drawback of very long setting times, which constitutes problems at surgery.

Another group of materials for substituting bone tissue in fracture sites and other bone defects is calcium phosphate cements. Due to their biocompatibility and their osteoconductivity they can be used for bone replacement and augmentation.

Hydroxylapatite, a crystalline substance which is the primary component of bone, is mainly used as a bone substitute, but is not strong enough for use under weight bearing conditions. Experiments have shown that hydroxy-lapatite cement forms a stable implant in respect of shape and volume over 12 months and has the same excellent tissue compatibility as exhibited by commercial ceramic hydroxylapatite preparations. Microscopic examination clearly demonstrated that hydroxylapatite cement was progressively ingrown by new bone over time.

Although the ideal is to achieve hydroxylapatite, there are also apatite-like calcium phosphates which can be obtained as potential bone substitutes. In Table 1 calcium phosphates are presented which are formed by a spontaneous precipitation at room or body temperature, as well as the pH range, within which these components are stable.

TABLE 1

Calcium phosphates obtained by precipitation at room or body temperature

| Ca/P | Formula | Name | pH |
|---|---|---|---|
| 0.5 | $Ca(H_2PO_4) \cdot H_2O$ | MCPM | 0.0-2.0 |
| 1 | $CaHPO_4 \cdot 2H_2O$ | DCPD | 2.0-6.0 |
| 1.33 | $Ca_8(HPO_4)_2(PO_4)_4 \cdot 5H_2O$ | OCP | 5.5-7.0 |
| 1.5 | $Ca_9(HPO_4)(PO_4)_5OH$ | CDHA | 6.5-9.5 |
| 1.67 | $Ca_5(PO_4)_3OH$ | PHA | 9.5-12 |

Other calcium phosphates can be obtained by means of sintering at high temperatures, above 1000° C. (Table 2). These calcium phosphates can not be obtained by precipitation in room or body temperature. However, they can be mixed with an aqueous solution alone or in combinations with other calcium phosphates to form a cement-like paste which will set with time.

TABLE 2

Components forming calcium phosphate cements

| Ca/P | Compound | Formula | Name |
|---|---|---|---|
| 1.5 | α-tricalcium phosphate | $\alpha\text{-}Ca_3(PO_4)_2$ | α-TCP |
| 1.5 | β-tricalcium phosphate | $\beta\text{-}Ca_3(PO_4)_2$ | β-TCP |
| 1.67 | Sintered hydroxylapatite | $Ca_{10}(PO_4)_6(OH)_2$ | SHA |
| 2.0 | Tetracalcium phosphate | $Ca_4(PO_4)_2O$ | TTCP |

Bone mineral substitute materials can be used for preparing a paste which can be injected directly into a fracture site. The paste is injected into the void in the bone and, upon hardening, an implant is obtained which conforms to the contours of the gap and supports the cancellous bone. Both calcium sulphate and hydroxylapatite materials have been extensively investigated as a possible alternative to autogenous bone grafts to help restore osseous defects of bone and fixation of bone fracture.

In this connection it is important that a complete stability is obtained as quickly as possible during or after surgery in order to prevent motions at site of healing. This especially applies to fractures, but also when filling of a bone cavity or replacing bone lost during tumor removal the healing is inhibited by movements and the ingrowth of new bone is prevented. Thus, the injected material must cure fast and adhere firmly to the bone tissue.

It is also of importance that the hardened material is so similar in structure to the bone so that it can be gradually resorbed by the body and replaced by new bone growth. This process can be facilitated if the hardened cement is provided with pores, which can transport nutrients and provide growth sites for new bone formation.

M. Bohner et al. disclosed at the Sixth World Bio-materials Congress Transactions (May 15-20, 2000) a method to obtain an open macroporous calcium phosphate block by using an emulsion of a hydrophobic lipid (oil) in an aqueous calcium phosphate cement paste or an emulsion of an aqueous calcium phosphate cement paste in oil. After setting, the cement block was sintered at 1250° C. for 4 hours. Likewise, CN 1193614 shows a porous calcium phosphate bone cement for repairing human hard tissue. The cement contains pore-forming agent which may be a non-toxic surfactant, or a non-toxic slightly soluble salt, acidic salt and alkaline salt.

Studies have also been made on mixtures of the above mentioned bone mineral substitute materials. In U.S. Pat. No. 4,619,655 is disclosed a bone mineral substitute material comprising a mixture of Plaster of Paris, i.e. calcium sulphate hemihydrate, and calcium phosphate ceramic particles, preferably composed of hydroxylapatite, or tricalcium phosphate or mixtures thereof. According to U.S. Pat. No. 4,619, 655 tests show that when alloplasts composed of 50/50 mixtures of hydroxylapatite/Plaster of Paris were implanted into experimentally created defects in rat mandible, the Plaster of Paris was completely resorbed within a few weeks and replaced by connective tissue. The hydroxylapatite was not resorbed and some particles were eventually completely surrounded by bone. It was therefore concluded that the Plaster of Paris acted as a scaffold for the incorporation of hydroxylapatite into bone.

A recent study presented on the "Combined Orthopaedic Research Societies Meetings", Sep. 28-30, 1998, Hamamatsu, Japan, also shows additional tests relating to mixtures of Plaster of Paris and hydroxylapatite. According to this study a combination of hydroxylapatite particles and Plaster of Paris had a viscosity which allowed an easy placement of the implant material and prevented migration of hydroxylapatite particles into surrounding tissues during and after implantation. The experiments showed that Plaster of Paris was absorbed in relatively short time, was easily manipulated with hydroxylapatite particles, and did not interfere with the process of bone healing.

WO 9100252 shows a composition which is capable of hardening in blood within about 10-45 min. The composition comprises essentially calcium sulphate hemihydrate with small amounts of calcium sulphate dihydrate. Organic and inorganic materials, such as hydroxylapatite, can also be included in the composition. After hardening, particles of hydroxylapatite are obtained within a calcium sulphate cement. The calcium sulphate cement is dissolved rapidly by aqueous body fluids within four weeks, leaving solid particles of hydroxylapatite.

Likewise, such particles of hydroxylapatite within a calcium sulphate cement are obtained by the method of WO 9117722. The composition for use as an animal implant comprises calcium sulphate hemihydrate, calcium phosphate, and sodium sulphate. The calcium phosphate is hydroxylapatite and the sodium sulphate enables the composition to be used in the presence of blood or other body fluids.

SUMMARY OF THE INVENTION

The object of the invention is to provide an injectable composition for a bone mineral substitute material with the capability of being hardened in a body fluid in vivo, which hardens during surgery with accompanying early control of fracture fragment movement as well as provides a stable lasting implant over a year with high mechanical strength, and which during this later period presents a porous as well as irregular structure for bone ingrowth.

A further object of the present invention is to provide such an improved injectable bone mineral substitute for filling defects in osteoporotic bone and for additional fracture fixation in substantially cancellous bone which does not exhibit the drawbacks of high viscosity at delivery and low fracture toughness.

Still another object of the invention is to provide an injectable bone mineral substitute having excellent biocompatibility, favorable biological and rheological properties. The bone mineral substitute should also be biodegradable and be possible to sterilize by radiation or gas without suffering a significant deterioration in properties.

In order to achieve these objects the injectable composition according to the invention has been given the characterizing features of claim 1.

According to the invention a composition is provided which comprises two types of bone cement materials, which both are subjected to a hardening reaction in contact with water.

A cement of hardened calcium sulphate (gypsum) will remain set in a dry environment. In a wet environment, such as in a Body Simulated Solution, this material will immediately start to disintegrate. Thus, an implanted material with reduced strength will be obtained in the body. The solid material obtained will start to degrade, eventually within 1-2 days.

On the other hand, in order to induce a setting (hardening) reaction in a Body Simulated Solution or in a body with its blood, saline can be used. By using saline a setting will be obtained immediately under any conditions, but the implant obtained will still degrade quite rapidly.

The second reaction, in which a calcium phosphate is hardened (cemented) to a calcium phosphate cement in the presence of water, will take longer time—about 18 h or more—in order to set to a high strength material. During this period of time the already set sulphate will confer an initial strength to the implant, and when the setting reaction of tricalcium phosphate to a high strength material is completed, a final strength will be obtained, which lasts for months or years.

In this connection the term "calcium phosphate cement" refers to the recognized definition (S. E. Gruninger, C. Siew, L. C Chow, A. O'Young, N. K. Tsao, W. E. Brown, *J. Dent. Res.* 63 (1984) 200) of a reaction product of a powder or a mixture of powders which—after mixing with water or an aqueous solution to a paste—at a temperature around room temperature or body temperature react with the formation of a precipitate, which contains crystals of one or more calcium phosphates and which sets by the entanglement of the crystals within the precipitate. Thus, different calcium phosphate products (calcium phosphate cements) can be obtained during the setting reaction in dependence on the component(s) of the powders used for the paste inventive injectable composition for a bone mineral substitute material.

BRIEF DESCRIPTION OF DRAWINGS

The invention will now be explained in more detail, reference being made to the accompanying drawings, in which.

DETAILED DESCRIPTION OF THE INVENTION

In order to accomplish an injectable bone mineral substitute material having improved characteristics, tests were made with the object to evaluate the effects of particle size, water content and accelerator on the viscosity, setting time and porosity of the injectable bone mineral substitute material of the invention.

The inventive injectable composition for a bone mineral substitute material comprises a dry powder mixed with an aqueous liquid. A main requirement on such a material is its setting time, which should be within 5-12 minutes. Additionally, the viscosity of the material should be adapted to render it injectable into the bone for 1-5 minutes after the beginning of the mixing procedure.

The evaluated materials comprised calcium sulphate hemihydrate, also known as Plaster of Paris. It was found that the addition of a small amount of finely ground already reacted calcium sulphate dihydrate, $CaSO_4 \cdot 2H_2O$, had a decisive impact on the setting time and the injectable time of the bone mineral substitute. Due to the addition of an accelerator the setting time period was considerably shortened while the injectable time was still long enough to make it possible to inject the material of the invention into e.g. a bone cavity. It is assumed that other accelerators and mixtures of accelerators may be used, e.g. starch, mixtures of calcium sulphate dihydrate and lignosulphate, calcium sulphate dihydrates having composite coatings, etc.

Those reactions which forms hydroxylapatite, i.e. precipitated hydroxylapatite (PHA) or calcium deficient hydroxylapatite (CDHA), can be classified into three groups. The first group consists of calcium phosphates, which are transformed into hydroxylapatite by a hydrolysis process in an aqueous solution (eq. 1-5).

$$5Ca(H_2PO_4) \cdot H_2O \rightarrow Ca_5(PO_4)_3OH + 7H_3PO_4 + 4H_2O \quad (1)$$

$$5CaHPO_4 \cdot 2H_2O \rightarrow Ca_5(PO_4)_3OH + 2H_3PO_4 + 9H_2O \quad (2)$$

$$5Ca_8H_2(PO_4)_6 \cdot 5H_2O \rightarrow 8Ca_5(PO_4)_3OH + 6H_3PO_4 + 17H_2O \quad (3)$$

$$5Ca_3(PO_4)_2 + 3H_2O \rightarrow 3Ca_5(PO_4)_3OH + H_3PO_4 \quad (4)$$

$$3Ca_4(PO_4)_2O + 3H_2O \rightarrow 2Ca_5(PO_4)_3OH + Ca(OH)_2 \quad (5)$$

Precipitated hydroxylapatite is the least soluble calcium phosphate at pH over 4,2. This means that any other calcium phosphate present in an aqueous solution at this pH range will tend to dissolve, with the precipitation of PHA as a product. This hydrolysis process ($Ca(OH)_2$—$H_3PO_4$—$H_2O$) is very slow due to a decrease in supersaturation as the reaction proceeds.

The only calcium phosphate which can react via a hydrolysis process to an apatite without the formation of sub-products is α-tricalcium phosphate (eq. 6), and the apatite formed in this reaction is a calcium deficient hydroxylapatite.

$$3\alpha\text{-}Ca_3(PO_4)_2 + H_2O \rightarrow Ca_9(HPO_4)(PO_4)_5OH \quad (6)$$

The second group of reactions to a hydroxylapatite, i.e. precipitated hydroxylapatite (PHA) or calcium deficient hydroxylapatite (CDHA), is the combinations between TTCP and other calcium phosphates. TTCP is the only calcium phosphate with Ca/P ratio above 1.67. Thus, this substance can be mixed with other calcium phosphates with lower Ca/P ratio to obtain PHA or CDHA without the formation of acids or bases as by-products. Theoretically, any calcium phosphate more acid than PHA can react directly with TTCP to form HA or CDHA according to the following chemical reactions.

$$7Ca_4(PO_4)_2O = 2Ca(H_2PO_4)_2 \cdot H_2O \rightarrow 6Ca_5(PO_4)_3OH + 3H_2O \quad (7)$$

$$2Ca_4(PO_4)_2O + Ca(H_2PO_4)_2 \cdot H_2O \rightarrow Ca_9(HPO_4)(PO_4)_5OH + 2H_2O \quad (8)$$

$$Ca_4(PO_4)_2O + CaHPO_4 \cdot 2H_2O \rightarrow Ca_5(PO_4)_3OH + 2H_2O \quad (9)$$

$$3Ca_4(PO_4)_2O = 6CaHPO_4 \cdot 2H_2O \rightarrow 2Ca_9(HPO_4)(PO_4)_5OH + 13H_2O \quad (10)$$

$$Ca_4(PO_4)_2O + CaHPO_4 \rightarrow Ca_5(PO_4)_3OH \quad (11)$$

$$3Ca_4(PO_4)_2O = 6CaHPO_4 \rightarrow 2Ca_9(HPO_4)(PO_4)_5OH + H_2O \quad (12)$$

$$3Ca_4(PO_4)_2O + Ca_8H_2(PO_4)_6 \cdot 5H_2O \rightarrow 4Ca_5(PO_4)_3OH + 4H_2O \quad (13)$$

$$3Ca_4(PO_4)_2O + 3Ca_8H_2(PO_4)_6 \cdot 5H_2O \rightarrow 4Ca_9(HPO_4)(PO_4)_5OH + 14H_2O \quad (14)$$

$$Ca_4(PO_4)_2O = 2Ca_3(PO_4)_2 + H_2O \rightarrow Ca_5(PO_4)_3OH \quad (15)$$

In equations (7) and (8) DCPD is formed as an intermediate reaction product, but with PHA or CDHA at the end of the reaction. Reactions (13), (14), and (15) are all very slow. However, by using the formulas (9)-(12) it is possible to produce a cement which sets and hardens with time at room or body temperature and at a neutral pH.

It is also possible to form PRA as the final hardened product by using mixtures of calcium phosphates with a Ca/P ratio of less than 1.67. This is accomplished by using additional calcium sources, such as $Ca(OH)_2$ or $CaCO_3$, instead of TTCP. One example is the reaction β-TCP+DCPD+$CaCO_3$→PHA. Initially formed crystals of PHA from a reaction between CDPD and $CaCO_3$ function as binders between β-TCP particles. When DCPD is consumed the reaction continues between the remaining calcium carbonate and β-TCP with the formation of PHA. However, it seems that the latter process has a detrimental effect on the mechanical strength of the cement.

It is preferred that the calcium phosphate with the capability of being hardened to a calcium phosphate cement when reacting with an aqueous liquid is tricalcium phosphate (TCP), tetracalcium phosphate (TTCP), anhydrous dicalcium phosphate, monocalcium phosphate monohydrate (MCPM), dicalcium phosphate dihydrate (DCPD), or octo-calcium phosphate (OCP). Preferably, the calcium phosphate is α-tricalcium phosphate.

In order to confer an initial strength to a bone mineral substitute material the calcium sulphate hemihydrate in the composition according to the invention should comprise 2-80 wt %, preferably 10-30 wt % of the dry powder to be mixed with an aqueous liquid. Likewise, the calcium phosphate to be hardened to a calcium phosphate cement should comprise 10-98 wt %, preferably 70-90 wt % of the dry powder. In the composition, the aqueous liquid should comprise between 0.1 and 2 ml, preferably between 0.5 and 1 ml per gram powder.

By preferably using particulate reaction components in the inventive composition, a high strength implant material will be obtained initially. The fast setting calcium sulphate material will be formed within a block of a slow setting material, i.e. the calcium phosphate cement. Thus, when initial strength decreases the second strength increases, and its final strength will be maintained within the body. Pores, holes and cavities will gradually be formed as the sulphate degrades, which acts like lacuna, and the finally set and hardened implant of a high strength material will look like a normal bone.

Both reactions in the inventive composition can be controlled by including an accelerator or a retarder. By using seed particles, the processes can be accelerated.

If such an accelerator is added, the calcium sulphate hemihydrate will set rapidly, i.e. within 10 min. Particulate calcium sulphate dihydrate is a suitable accelerator for this reaction, the particle size being less than 1 mm. A more efficient reaction is obtained if the particulate calcium sulphate dihydrate has a particle size of less than 150 μm, preferably less than 100 μm, and most preferable less than 50 μm. The particulate calcium sulphate dihydrate should comprise between 0.1 and 10 wt %, preferably between 0.1 and 2 wt % of the calcium sulphate hemihydrate which is to react with an aqueous liquid. The accelerator should be adapted so that a set material is obtained within 15 min, preferably within 8 min which has a threshold strength of about 30 MPa in a clinical situation. Preferably, the partitulate calcium sulphate dihydrate is α-calcium sulphate dihydrate.

The second reaction of a calcium phosphate to a calcium phosphate cement sets slowly, but can be controlled to set within 18 h as a bone mineral substitute material with a strength of about 30 MPa. This can be accomplished by adding hardened particulate calcium phosphate cement to the inventive composition. The hardened calcium phosphate cement can be hydroxylapatite (HA), preferably precipitated hydroxylapatite (PHA), tricalcium phosphate (TCP), or a mixture thereof. It should have a Ca/P ratio between 1.5 and 2. The particulate calcium phosphate cement should have a particle size which is less than 20 μm, preferably less than 10 μm and comprise between 0.1 and 10 wt %, preferably between 0.5 and 5 wt % of the calcium phosphate which is to react with an aqueous liquid.

The reaction of calcium phosphate to a calcium phosphate cement can also be accelerated by a phosphate salt, for example disodium hydrogen phosphate ($Na_2HPO_4$), which is dissolved in the aqueous liquid. In this case, the accelerator should be present in the aqueous liquid at concentrations of 0.1-10 wt %, preferably 1-5 wt %.

The two types of accelerator for the reaction of calcium phosphate to calcium phosphate cement can be used either separately or in combination.

In the composition according to the invention the aqueous liquid can be distilled water or a balanced salt solution, such as PBS, PBSS, GBSS, EBSS, HBSS, or SBF.

The injectability of the composition according to the invention can be improved in several ways. It has surprisingly been shown that a pH reducing component can be added to the inventive composition, the injectability thereof being improved. Such a pH reducing component is for example ascorbic acid or citric acid. These acids are included in the sterile liquid or the sterile powder of the composition in amounts of 0.1-5 wt %, preferably 0.5-2 wt %.

Another way to improve the injectability of the composition is to add a biologically compatible oil. The concentration of the oil should be between 0.1 and 5 wt %, preferably between 0.5 and 2 wt %. A suitable oil to be used in the inventive composition is vitamin E. The oil can either be intermixed with the sterile powder or included in the sterile liquid of the composition.

As stated above, the addition of a small amount of already reacted calcium sulphate dihydrate had an effect on the injectable time of the bone mineral substitute. Thus, by replacing some of the non-reacted calcium sulphate hemihydrate with reacted calcium sulphate dihydrate, the injectability of the composition could be improved. As much as 95% of the hemihydrate can be replaced. Preferably, 50-90% of the hemihydrate is replaced by the dihydrate, most preferred 80-90%.

In order to further improve the bone mineral substitute material obtained with the inventive composition it is possible to further include additional substances, e.g. growth factors, anti-cancer substances, antioxidants and/or antibiotics, etc. Antibiotic containing bone cement is already known and it has been shown that addition of antibiotics to synthetic hydroxylapatite and cancellous bone releases said antibiotics in a concentration sufficient for treating bone infections when said substances are administered into the bone.

An efficient mixing system must be available in order to prepare the composition according to the invention. The mixing can take place in a conventional cement mixing system and the composition is injected by means of a convenient delivery system. The mixing container is preferably of that type which can suck the aqueous component into the powder component (German Patent 4409610). This Prepack™ system is a closed mixing system for delivery in combination with prepacked components in a flexible foil bag. Other mixing devices can of course also be used, for example two interconnected soft bags which can be adapted to a delivering cylinder.

The formation of air bubbles in the composition, which can interfere with the hardening reaction of the calcium sulphate hemihydrate and result in a decreased initial mechanical strength of the implanted material during surgery, can be prevented by mixing the composition under conditions of subatmospheric pressure, e.g. in vacuo. However, an atmospheric pressure can also be used. Preferably, the powder component of the composition is sterilized by means of radiation before it is mixed with the sterile liquid component.

EXAMPLES

The invention will now be further described and illustrated by reference to the following examples. It should be noted, however, that these examples should not be construed as limiting the invention in any way.

Comparative Example 1

As a control test the injectable time and the setting time of pure calcium sulphate hemihydrate were determined to be more than 10 and 20 minutes, respectively.

Comparative Example 2

As a second control test the injectable time and the setting time of a mixture of calcium sulphate hemihydrate, and hydroxylapatite were also determined to be more than 10 and 20 minutes, respectively.

Comparative Example 3

The injectable time (IT) and the setting time (SI) were studied for the first reaction of a calcium sulphate hemihydrate to calcium sulphate dihydrate in the presence of a passive additive. Twenty different mixtures of calcium sulphate hemihydrate, hydroxylapatite (HA) and accelerator (Acc) were evaluated, which had different ratios of hydroxylapatite and accelerator, see Table 3. The setting time was determined by a mechanical test. A metallic rod having a weight of 23 g, a diameter of 10 mm and a length of 35 mm was dropped from a height of 35 mm. The time when the rod did not leave any mark on the sample was registered as the setting time.

TABLE 3

| TEST NO. | $CASO_4$ (G) | HA (G) | HA (%) | ACC (%) | IT (MIN) | SI (MIN) |
|---|---|---|---|---|---|---|
| 1 | 32 | 4 | 10 | 10 | 1.5 | 3.0 |
| 2 | 28 | 8 | 20 | 10 | 1.5 | 4.0 |
| 3 | 24 | 12 | 30 | 10 | 1.5 | 4.0 |
| 4 | 20 | 16 | 40 | 10 | 2.0 | 6.0 |
| 5 | 16 | 20 | 50 | 10 | 1.5 | 6.0 |
| 6 | 34 | 4 | 10 | 5 | 2.0 | 5.0 |
| 7 | 30 | 8 | 20 | 5 | 1.5 | 5.0 |
| 8 | 26 | 12 | 30 | 5 | 2.5 | 7.0 |
| 9 | 22 | 16 | 40 | 5 | 2.5 | 7.5 |
| 10 | 18 | 20 | 50 | 5 | 2.0 | 7.0 |

TABLE 3-continued

| TEST NO. | CASO$_4$ (G) | HA (G) | HA (%) | ACC (%) | IT (MIN) | SI (MIN) |
|---|---|---|---|---|---|---|
| 11 | 35 | 4 | 10 | 2.5 | 1.5 | 5.0 |
| 12 | 31 | 8 | 20 | 2.5 | 1.5 | 5.0 |
| 13 | 27 | 12 | 30 | 2.5 | 2.0 | 7.5 |
| 14 | 23 | 16 | 40 | 2.5 | 2.5 | 7.5 |
| 15 | 19 | 20 | 50 | 2.5 | 2.5 | 10.0 |
| 16 | 35.6 | 4 | 10 | 1 | 2.5 | 7.0 |
| 17 | 31.6 | 8 | 20 | 1 | 3.0 | 9.0 |
| 18 | 27.6 | 12 | 30 | 1 | 3.5 | 10.5 |
| 19 | 23.6 | 16 | 40 | 1 | 4.0 | 13.0 |
| 20 | 19.6 | 20 | 50 | 1 | 4.0 | 14.5 |

Example 1

Different bi-phasic injectable cements were produced, which were based on α-tricalcium phosphate and α-calcium sulphate hemihydrate.

The mechanical strength of each cement produced was evaluated with time at 10 hours, 24 hours, 3 days, and 14 days after mixing of the cement with water. The evaluation was performed at the time periods given by means of a cylindrical specimen (d=6 mm, h=12 mm) that had been immersed in a physiological saline solution of 37° C. The results are shown in Table 4 below.

TABLE 4

| Amount of α-TCP | Compressive strength 10 h | | Compressive strength 24 h | | Compressive strength 3 d | | Compressive strength 14 d | |
|---|---|---|---|---|---|---|---|---|
| (wt %) | (MPa) | ± S.D. | (MPa) | ± S.D. | (MPa) | ± S.D. | (MPa) | ± S.D. |
| 0 | 11 | 3.63 | 7.64 | 1.41 | 12.99 | 2.66 | 9.66 | 3.2 |
| 20 | 1.01 | 0.39 | 1.69 | 0.49 | 3.99 | 0.35 | 5.36 | 0.33 |
| 40 | 0.68 | 0.25 | 5.08 | 1.66 | 8.82 | 1.2 | 9.82 | 1.86 |
| 60 | 3.58 | 1.02 | 5.1 | 0.91 | 15.73 | 5.24 | 14.13 | 1.42 |
| 80 | 5.31 | 1.03 | 10.72 | 0.69 | 21.8 | 3.41 | 23.92 | 3.06 |
| 100 | 6.24 | 1.48 | 22.37 | 6.34 | 37.99 | 4.74 | 33.98 | 10.37 |

Example 2

The compressive strength was further tested with reference to α-TCP containing less than 20 wt % calcium sulphate hemihydrate (CSH). (CSH was obtained from Bo Ehrlander AB, Gothenborg, Sweden.)

The two powders were mixed together mechanically during 5 min. Then, the liquid was added to the powder at a liquid to powder (L/P) ratio of 0.32 ml·g$^{-1}$. The liquid contained 2.5 wt % Na$_2$HPO$_4$ as an accelerator.

Moulds were then filled and immersed in a saline solution (0,9%) at 37° C. for 7 days. The results are shown in Table 5 below and in FIG. 1.

Figure 1:
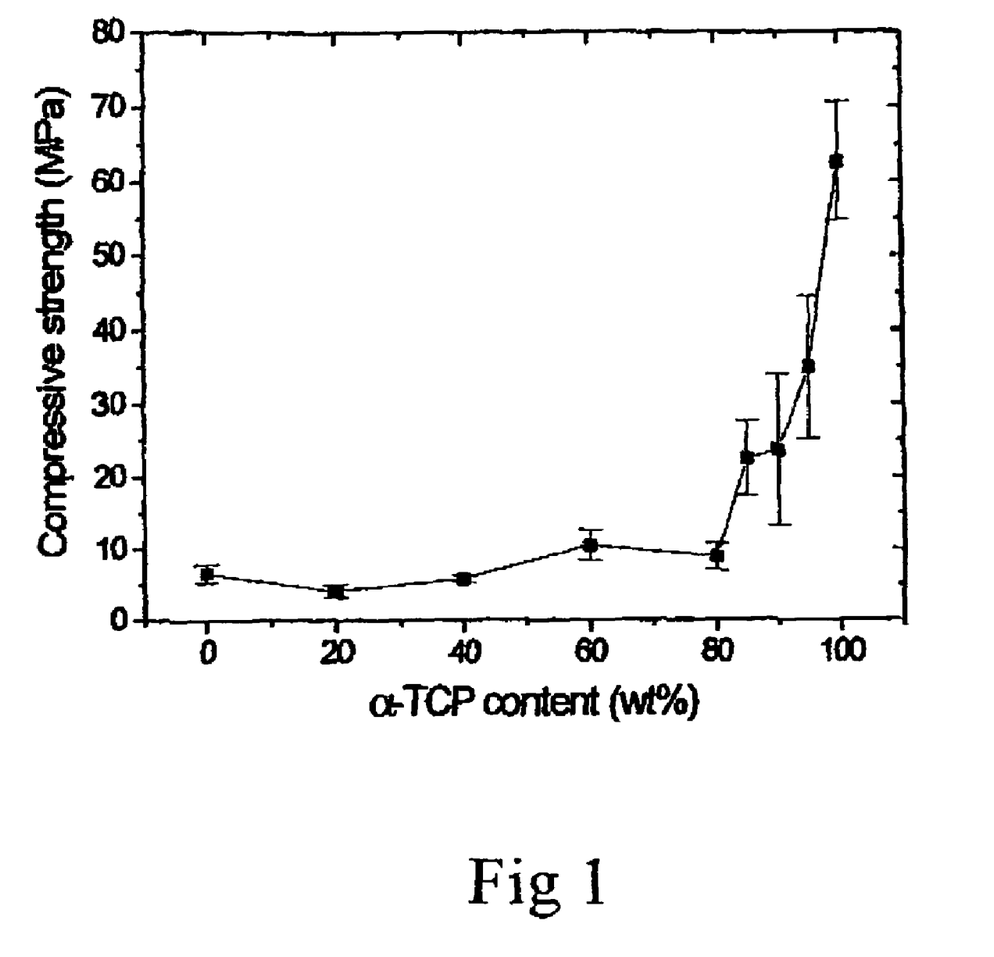
FIG. 1 shows the effects of α-tricalcium phosphate on compressive strength.

As seen in FIG. 1, the compressive strength was drastically increased when the α-TCP content exceeded 80 wt %.

TABLE 5

| Content of CSH (wt %) | Compressive strength (MPa) | Standard Deviation (MPa) | No. of samples tested |
|---|---|---|---|
| 0 | 62.62 | 7.98 | 7 |
| 5 | 34.80 | 9.65 | 7 |

TABLE 5-continued

| Content of CSH (wt %) | Compressive strength (MPa) | Standard Deviation (MPa) | No. of samples tested |
|---|---|---|---|
| 10 | 23.54 | 10.37 | 8 |
| 15 | 22.45 | 5.12 | 10 |

Example 3

During each of the two setting reactions, crystals are formed when calcium sulphate hemihydrate and calcium phosphate, respectively, react with water in the setting reactions. Initially, crystal nuclei are created and the final crystal structure is then formed by growth from the nuclei. By adding already formed crystals of set material, the nucleation step in the setting process is already completed, which will decrease the time needed to crystallize the material and make it hard. The crystals will grow directly from particles of added calcium sulphate dihydrate and hydroxylapatite, respectively. Thus, these added particles of set material will act as accelerators in the setting reactions.

The staller size of accelerator particles added to the material, the more efficient accelerating effect will be obtained because the crystals will grow from the surface of the particles. It the accelerator particles are small, then the surface of the particles will be large per unit of weight.

When α-CaSO$_4$.2H$_2$O is used as an accelerator it will be more efficient than β-CaSO$_4$.2H$_2$O when α-CaSO$_4$.½H$_2$O is used as the main component of the material. This could be explained by the crystal shape difference between the two forms of the calcium sulphate. Since the crystals are growing directly from the particle surface of the accelerator, the reaction proceeds faster if the accelerator crystals have exactly the same shape as the crystals that are forming from the main component of the material.

Example 4

Figure 2:
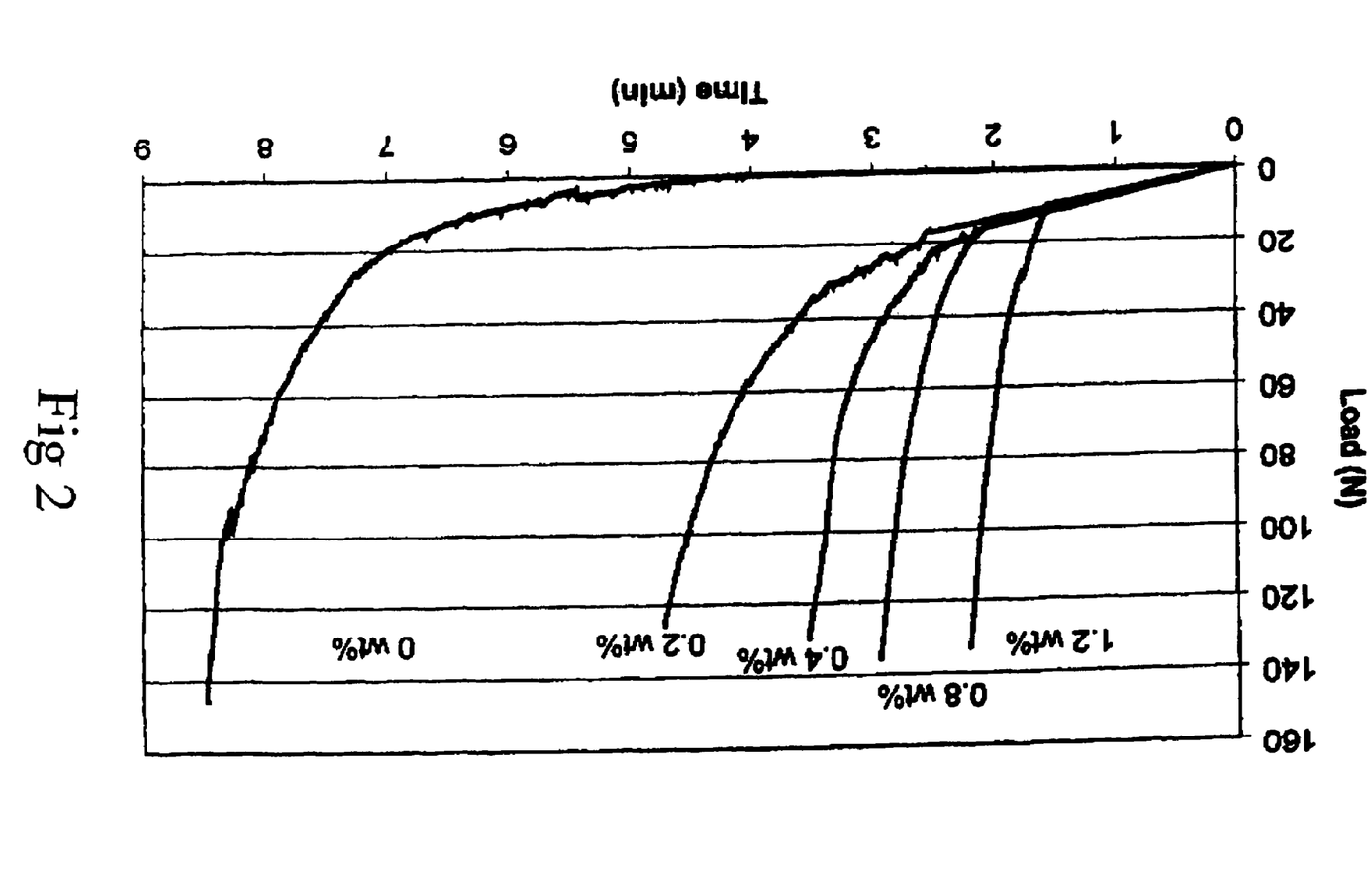
FIG. 2 shows the effects of the content of calcium sulphate dihydrate on the injection time.

The effects of the content of calcium sulphate dihydrate on the injection time is shown in FIG. 2. In this case the liquid/powder (L/P) ratio is 0.4 ml/g. The limit of injection time was defined when the load reached N, which is comparable to the highest force by hand at which injection was possible.

Example 5

Figure 3:
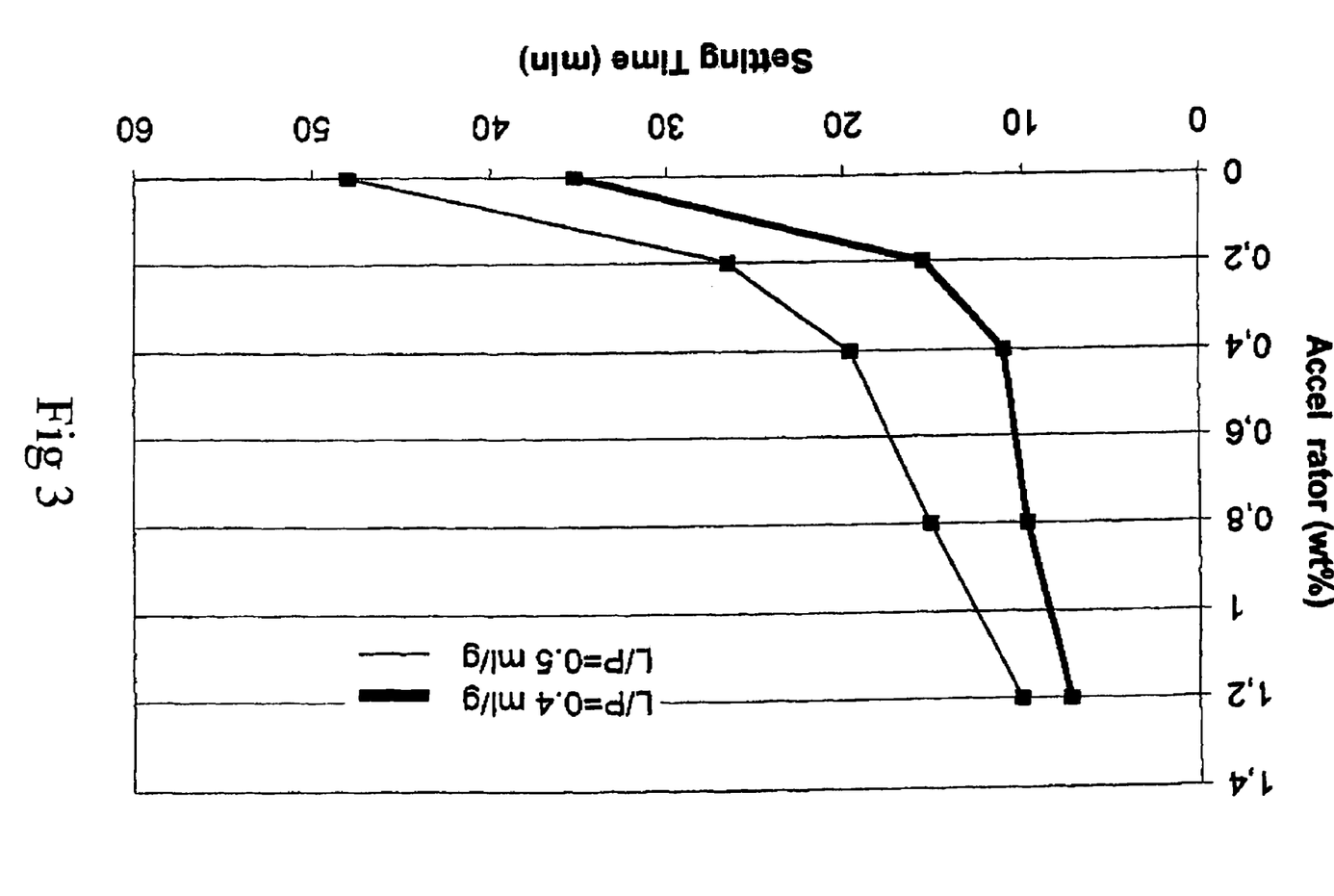
FIG. 3 shows the effects of the water content and the content of calcium sulphate dihydrate on the setting time.

The effects of the water content and the content of calcium sulphate dihydrate on the setting time is shown in FIG. 3, wherein L/P is the liquid-powder ratio (ml/g). The setting time was measured by using Gillmore Needles according to ASTM Standard C266.

Example 6

In the inventive composition, the form of the calcium sulphate hemihydrate is of importance. α-Calcium sulphate hemihydrate ($\alpha$-$CaSO_4 \cdot \frac{1}{2}H_2O$) is advantageous to use because of its mechanical strength. $\alpha$-$CaSO_4 \cdot \frac{1}{2}H_2O$ has a compressive strength of 40.4 MPa compared with 14 MPa for β-$\alpha$-$CaSO_4 \cdot \frac{1}{2}H_2O$.

Example 7

Biodegradation of the Calcium Sulphate with Hydroxylapatite Bone Substitute in vitro and in vivo.

The degradation rate of calcium sulphate with 40 wt % hydroxylapatite was investigated. The material was placed in a Simulated Body Fluid as well as muscle pockets in rats. The mechanical strength and size of the block obtained were investigated with time as a biodegradation index.

Mechanical Testing

Compressive strength testing was performed using an MTS and Instron 8511.20 testing equipment. After harvesting the materials, the samples were directly placed between self-levelling platens and compressed at 1 mm min$^{-1}$ until failure at room temperature.

Volume Measurements

After the material harvesting, a caliper measured the volume of the block of material.

In Vitro Study

Cements of calcium sulphate or calcium sulphate with hydroxylapatite were prepared by mixing with distilled water at L/P ratio of 0.25 ml/g. After mixing the cement was injected into a PFTE mould and allowed to set. The samples were 4 mm in diameter and 8 mm in length. Six cylindrical samples were placed in a Simulated Body Fluid, and the liquid was changed every day. After one week the samples were directly placed between self-levelling platens and subjected to compressive strength testing until failure at room temperature.

In Vivo Study

Materials Preparation

Calcium sulphate hemihydrate ($CaSO_4 \cdot \frac{1}{2}H_2O$) was mixed with 40 wt % hydroxylapatite powder ($Ca_{10}(PO_4)_6(OH)_2$; HA). The mixture of POP-HA was sintered and quenched in air. An accelerator (a calcium sulphate) was added at 0.4 wt % to the POP-HA, and the dry powder material was sterilized by gamma-irradiation.

A cement was prepared by mixing the powder with distilled water at a L/P ratio of 0.25 ml/g. Materials were prepared, which contained calcium sulphate or calcium sulphate+hydroxylapatite. After mixing, the cement was injected into a PFTE mould and allowed to set. The samples were cylindrical with diameter of 4 mm and height of 8 mm. Once set, the samples are inserted into muscle pockets of rats.

Animals

Sprague-Dawley rats weighing around 200 g were used and kept in animal facilities for 1 week before use. The animals were fed a standard laboratory diet. All rats were anesthetized with peritoneal injections of 0.5-0.6 ml of a solution containing 1 ml pentobarbital (60 mg/ml), 2 ml diazepam (5 mg/ml), and 1 ml saline (0.15 M). The implants were inserted in muscles of the rats. Nine rate were used for each period studied. The rats were killed by a peritoneal injection of an overdose of pentobarbital at 1 or 4 weeks after implantation.

Results

After one week of incubation the mechanical strength was recorded of the cylindrical samples placed in the Simulated Body Fluid or muscles pockets in rats, respectively. The mechanical strength of the materials had decreased from 35 Mpa to about 5 Mpa both in vitro as well as in vivo. The volume of remaining block was only ⅓ to ¹⁄₁₀ of the original block volume (Table 5).

After 4 weeks of incubation, the mechanical strength of the materials had totally disappeared, and the rods of calcium sulphate were almost completely absorbed. The calcium sulphate with hydroxylapatite was still present but totally deformed, and the material was surrounded by normal soft tissue. The tissue also penetrated into the materials. Furthermore, the mass of remaining material was larger than the original block implanted.

Table 6 below shows the volume of remaining cylinder material (Mean±SE) in rat muscles after an incubation of 1 or 4 weeks. The original volume of the cylinder material was 100 mm$^3$. Statistic analysis was performed by using the one way ANOVA method and Student's t~test. All results obtained exhibited a high statistical significance (p<0.0001).

TABLE 6

| | 1 week incubation | | 4 weeks incubation | |
|---|---|---|---|---|
| Material | No. of samples | Volume (mm$^3$) | No. of samples | Volume (mm$^3$) |
| PoP | 9 | 31.7 ± 3.1 | 9 | 1.9 ± 1.5 |
| PoP + HA | 9 | 6.1 ± 1.5 | 8 | 159.4 ± 21.7 |
| PoP + HA + Vitamin E | 8 | 9.1 ± 2.0 | 8 | 196.0 ± 17.9 |

The implanted material comprising calcium sulphate and hydroxylapatite was rapidly degraded within one week in both Simulated Body Fluid and in rats. The rate of degradation was the same in Simulated Body Fluid or muscles pockets indicating that only one method is needed in order to demonstrate the degradation rate.

In conclusion, tests of the combined sulphate and phosphate material exhibit biodegradation in vitro and in vivo as well as hardening of both components with good results with reference to injectability and setting.

The invention claimed is:

1. A composition for a bone mineral substitute material comprising a dry powder, the dry powder comprising a first setting reaction component, which is a calcium sulphate hemihydrate;
   a second setting reaction component, which is a calcium phosphate; and
   at least one particulate accelerator for the setting reaction of both the first and the second setting reaction components, wherein the at least one accelerator for the reaction of the first setting reaction component is particulate calcium sulphate dihydrate, and the at least one accelerator for the reaction of the second setting reaction component is hardened particulate calcium phosphate cement.

2. The composition of claim 1, wherein the calcium sulphate hemihydrate is an α-calcium sulphate hemihydrate.

3. The composition of claim 1, wherein the calcium phosphate is a tricalcium phosphate.

4. The composition of claim 1, wherein the particulate calcium phosphate cement has a Ca/P ratio between 1.5 and 2.

5. The composition of claim 1, wherein the particulate calcium phosphate cement is hydroxylapatite (HA), tricalcium phosphate (TCP), or a mixture thereof.

6. The composition of claim 5, wherein the hydroxylapatite is precipitated hydroxylapatite (PHA).

7. The composition of claim 1, wherein the particulate calcium phosphate cement has a particle size which is less than 20 µm.

8. The composition of claim 7, wherein the particulate calcium phosphate cement has a particle size which is less than 10 µm.

9. The composition of claim 1, wherein the particulate calcium phosphate cement comprises 0.1 wt % to 10 wt % of the calcium phosphate.

10. The composition of claim 9, wherein the particulate calcium phosphate cement comprises 0.5 wt % to 5 wt % of the calcium phosphate.

11. The composition of claim 1, wherein at least one of the calcium sulfate hemihydrate or the calcium phosphate reaction component is in particulate form with a particle size of 1 µm to 100 µm.

12. The composition of claim 11, wherein the particle size is 1 µm to 10 µm.

13. The composition of claim 3, wherein the tricalcium phosphate is α-tricalcium phosphate.

14. The composition claim 1, wherein the particulate calcium sulphate dihydrate is α-calcium sulphate dihydrate.

15. The composition of claim 14, wherein the particulate calcium sulphate dihydrate has a particle size less than 1 mm.

16. The composition of claim 15, wherein the particulate calcium sulphate dihydrate has a particle size less than 150 µm.

17. The composition of claim 16, wherein the particulate calcium sulphate dihydrate has a particle size less than 50 µm.

18. The composition of claim 1, wherein the particulate calcium sulphate dihydrate comprises 0.1 wt % to 10 wt % of the first reaction component.

19. The composition of claim 18, wherein the particulate calcium sulphate dihydrate comprises 0.1 wt % to 2 wt % of the first reaction component.

20. The composition of claim 1, wherein the calcium sulfate hemihydrate comprises 2 wt % to 80 wt % of the dry powder.

21. The composition of claim 20, wherein the calcium sulfate hemihydrate comprises 10 wt % to 30 wt % of the dry powder.

22. The composition of claim 1, wherein the calcium phosphate reaction component comprises 10 wt % to 98 wt % of the dry powder.

23. The composition of claim 22, wherein the calcium phosphate reaction component comprises 70 wt % to 90 wt % of the dry powder.

24. The composition of claim 1, further comprising a biologically active substance.

25. The composition of claim 24, wherein the biologically active substance comprises a growth factor, an anti-cancer substance, an antibiotic, and an antioxidant, and mixtures thereof.

26. A composition for a bone mineral substitute material comprising a dry powder, the dry powder comprising
a first setting reaction component, which is a calcium sulphate hemihydrate;
a second setting reaction component, which is a calcium phosphate;
at least one accelerator for the setting reaction of the first or second setting reaction component, or both the first and the second setting reaction components, wherein the at least one accelerator is chosen from at least one accelerator for the reaction of the first setting reaction component, wherein the accelerator is particulate calcium sulphate dihydrate, and the at least one accelerator for the reaction of the second setting reaction component, wherein the accelerator is hardened particulate calcium phosphate cement; and
a biologically compatible oil to improve the injectability of the composition.

27. The composition of claim 26, wherein the calcium sulphate hemihydrate is an α-calcium sulphate hemihydrate.

28. The composition according to claim 26, wherein the calcium phosphate is a tricalcium phosphate.

29. The composition according to claim 26, wherein the biologically compatible oil is vitamin E.

30. The composition according to claim 26, wherein the biologically compatible oil comprises 0.1 wt % to 5 wt % of the composition.

31. The composition according to claim 30, wherein the biologically compatible oil comprises 0.5 wt % to 2 wt % of the composition.

32. A composition for a bone mineral substitute material comprising
a dry powder, the dry powder comprising a first setting reaction component, which is a calcium sulphate hemihydrate;
a second setting reaction component, which is a calcium phosphate;
at least one accelerator for the setting reaction of the first or the second setting reaction component, or both the first and the second setting reaction components, wherein the at least one accelerator is chosen from at least one accelerator for the reaction of the first setting reaction component, the accelerator being a particulate calcium sulphate dihydrate, and at least one accelerator for the reaction of the second setting reaction component, the accelerator being a hardened particulate calcium phosphate cement; and
a pH reducing component to improve the injectability of the composition.

33. The composition of claim 32, wherein the calcium sulphate hemihydrate is an α-calcium sulphate hemihydrate.

34. The composition of claim 32, wherein the calcium phosphate is a tricalcium phosphate.

35. The composition of claim 32, wherein the pH reducing component is ascorbic acid or citric acid.

36. The composition of claim 32, wherein the pH reducing component comprises 0.1 wt % to 5 wt % of the composition.

37. The composition of claim 36, wherein the pH reducing component comprises 0.5 wt % to 2 wt % of the composition.

38. A kit for use in preparing a composition for a bone mineral substitute material, said kit comprising:
(1) the composition according to claim 1; and
(2) optionally an aqueous liquid.

39. The composition of claim 1, wherein the composition further comprises an aqueous liquid.

40. The composition of claim 39, wherein the aqueous liquid comprises between 0.1 ml and 2 ml per gram of the dry powder.

41. The composition of claim 40, wherein the aqueous liquid comprises between 0.5 ml and 1 ml per gram of the dry powder.

42. The composition according to claim 39, wherein the aqueous liquid comprises distilled water or a balanced salt solution.

43. The composition of claim 39, wherein the composition is contacted with the aqueous liquid and is capable of being hardened in a body fluid in vivo to a bi-phasic cement implant that with time obtains a porous structure for bone ingrowth.

44. A composition for a bone mineral substitute material comprising a dry powder, the dry powder comprising a first setting reaction component, which is a calcium sulphate hemihydrate;
   a second setting reaction component, which is a calcium phosphate; and
   at least one particulate accelerator for the setting reaction of both the first and the second setting reaction components, wherein the at least one accelerator for the reaction of the first setting reaction component is particulate calcium sulphate dihydrate, and the at least one accelerator for the reaction of the second setting reaction component is hardened particulate calcium phosphate cement, wherein the calcium sulphate dihydrate comprises 0.1 wt % to 10 wt % of the first reaction component.

45. A composition for a bone mineral substitute material according to claim 44, wherein the calcium sulphate dihydrate comprises 0.1 wt % to 2 wt % of the first reaction component.

* * * * *

UNITED STATES PATENT AND TRADEMARK OFFICE
CERTIFICATE OF CORRECTION

PATENT NO. : 7,417,077 B2
APPLICATION NO. : 10/333026
DATED : August 26, 2008
INVENTOR(S) : Lars Lidgren et al.

Page 1 of 1

It is certified that error appears in the above-identified patent and that said Letters Patent is hereby corrected as shown below:

On the title page, item (57), line 7, "comprise" should read --comprises--.

In claim 14, column 13, line 28, "composition claim" should read --composition of claim--.

Signed and Sealed this

Twenty-fifth Day of November, 2008

JON W. DUDAS
*Director of the United States Patent and Trademark Office*